United States Patent [19]
Sieben et al.

[11] Patent Number: 6,104,495
[45] Date of Patent: Aug. 15, 2000

[54] MEASURING APPARATUS

[75] Inventors: Ulrich Sieben, Reute; Bernhard Wolf, Stegen, both of Germany

[73] Assignee: Micronas Intermetall GmbH, Freilburg, Germany

[21] Appl. No.: 09/086,111

[22] Filed: May 27, 1998

[30] Foreign Application Priority Data

May 28, 1997 [DE] Germany .............................. 197 22 371
Jul. 19, 1997 [DE] Germany .............................. 197 31 078

[51] Int. Cl.⁷ .................................................. G01N 21/59
[52] U.S. Cl. ........................................ 356/432; 435/288.7
[58] Field of Search ........................ 356/432; 435/288.7; 422/82.09

[56] References Cited

U.S. PATENT DOCUMENTS

| | | | |
|---|---|---|---|
| 5,278,048 | 1/1994 | Parce et al. | 436/29 |
| 5,403,722 | 4/1995 | Floeder et al. | |
| 5,702,915 | 12/1997 | Miyamoto | 435/288.7 |
| 5,851,489 | 12/1998 | Wolf et al. | 422/82.02 |

FOREIGN PATENT DOCUMENTS

| | | |
|---|---|---|
| 0751393 | 1/1997 | European Pat. Off. . |
| 19512117 | 10/1996 | Germany . |
| 4417078 | 4/1998 | Germany . |
| 9109300 | 6/1991 | WIPO . |
| 9531716 | 11/1995 | WIPO . |

OTHER PUBLICATIONS

Sharonov, et al., "Confocal Spectral Imaging Analysis In Studies Of The Spatial Distribution Of Antitumor Drugs Within Living Cancer Cells", Analytica Chimica Acta, vol. 290, pp. 40–47, 1994.

Wittrup, et al., "Fluorescence Array Detector For Large-Field Quantitative Fluorescence Cytometry", Cytometry, vol. 19, pp. 206–213, 1994.

*Primary Examiner*—Richard A. Rosenberger
*Attorney, Agent, or Firm*—Arthur L. Plevy

[57] ABSTRACT

A measuring apparatus (1) for measuring physiological and/or chemical and/or physical properties of at least one living cell (3) contains, in addition to further sensors (4.1, 4.2), a plurality of optical sensors (4) on a support (2), particularly a support made of semiconductor material. By means of a controller (6) and a switching facility (8) which are integrated on the same support (2), the individual optical sensors (4) and the further sensors (4.1, 4.2) can be selectively interrogated. An external signal-analyzing facility (7) with a screen represents a sort of near-field microscope.

17 Claims, 2 Drawing Sheets

MEASURING APPARATUS

This invention relates to a measuring apparatus for measuring physiological and/or chemical and/or physical properties of at least one living cell which is coupled with the measuring apparatus such that it is immobilized. To this end, the cell is caused to unite with a support having a plurality of sensors for measuring the individual cell parameters. The material of the support is preferably a semiconductor material. Measuring apparatuses with such sensors are described, for example, in WO 95/31716 (internally: C-DIT-1678) or in DE 195 12 117 A1 (internally: C-DIT-1680). The prior-art arrangements are disadvantageous in that the living cells are observed through an optical microscope, so that the measuring apparatus is open at one end or must have at least one optical window. This requires a relatively complex and costly measuring structure which is made in part of transparent material, particularly glass or optical plastic. In addition, open measuring structures must be in a horizontal position, because otherwise liquids may leak out. This complicates the combination with physiological sensors, which measure properties of living cells via electronic signals and are generally made of nontransparent semiconductor materials.

It is therefore an object of the invention to enable simple optical access to the living cells in order to examine their current condition and particularly detect any metamorphic reaction during the measuring process. The change of the three-dimensional form of the cell may represent important additional information for the test or examination result which is difficult to obtain otherwise.

According to the characterizing features of claim 1, this object is attained by providing a measuring apparatus wherein:

at least part of the sensors are optical sensors arranged in the form of a matrix array, with the size of the array being at least equal to that of the area on the support which is to be occupied by one of the living cells;

an electronic switching facility is connected to the optical sensors for selectively sampling the outputs of the optical sensors and feeding them to a signal-analyzing facility; and the switching facility receives control signals from a controller.

The basic idea of the invention is to interpose an electrooptical medium between the cell to be observed and the observer. Especially suited for this purpose are miniaturized electrooptical sensors, which can be located very close to the cell and are suitable for integration with other sensors, which may be ion-sensitive or material-sensitive, for example, on a single semiconductor substrate serving as a support. Such an arrangement represents an electrooptical near-field microscope. If the support for the cells and the sensors is formed from a semiconductor material suitable for monolithic integration, a monolithic integrated circuit can be produced on the same substrate, so that preprocessing can take place in the immediate vicinity of the object. An "intelligent" sensor device is thus provided which has substantially greater performance capability than purely passive sensors. It is at least possible to process the electronic output signals from the electrooptical sensors by means of the integrated circuit in such a way that they can be externalized relatively easily via output circuits and terminals. The preprocessing may consist, for example, of a digitization of the analog sensor or measurement signals and their conversion into a suitable data stream. Further processing steps are possible by which the amount of data can be reduced, for example, or which serve to perform external processing and drive a display. Thus, the remaining analysis of the optical and other signals and their display can take place via a personal computer (PC). The associated devices on the substrate are controlled by control signals from a controller which may be formed, in whole or in part, on the substrate or is connected externally.

Analyzing the optical signals via a commercially available computer has an added advantage in that extensive automation of the image evaluation as well as image storage are possible using suitable programs, so that the observer has possibilities quite different from simple microscope observation. Through the image storage, for example, fast-motion evaluation or an arbitrarily frequent repetition of particular image sequences becomes possible in a simple manner. With a sufficient density of the electrooptical sensors, the display screen serves as a perfect microscope substitute, with the observation of the screen being less fatiguing than microscope observation, since the viewing distance is variable.

The cell is illuminated by an illuminant which is optically and mechanically coupled to the optical sensors in such a way that a radiation field is produced in the direction of the optical sensors, with the distance of the illuminant from the optical sensors being as small as possible. The distance must remain sufficient so as not to hinder the cells on the substrate. The illuminant may advantageously consist of a plurality of point sources of radiation which are activatable individually or in groups by means of the controller. This makes it possible to analyze the three-dimensional form of the cell, e.g. by means of different shadow zones. A similar effect will be obtained if the distance between the illuminant and the optical sensors is variable in a defined manner via an electronically controllable actuator.

The point sources of radiation, which are constituted, for example, by bundled optical fibers or miniaturized light-emitting diodes or are implemented in another manner, are advantageously arranged in linear form or in the form of a matrix array. To be able to examine particular structural features of the cell, it may be advantageous to use variable-frequency sources of radiation or sources of radiation of different frequencies. Accordingly, on the sensor side, not only different sensors for the physiological and/or chemical and/or physical measurements, but also different or variable-frequency or switchable sensors are provided for the optical evaluation.

The invention and preferred embodiments thereof will now be explained in more detail with reference to the accompanying drawings, in which.

Figure 1:
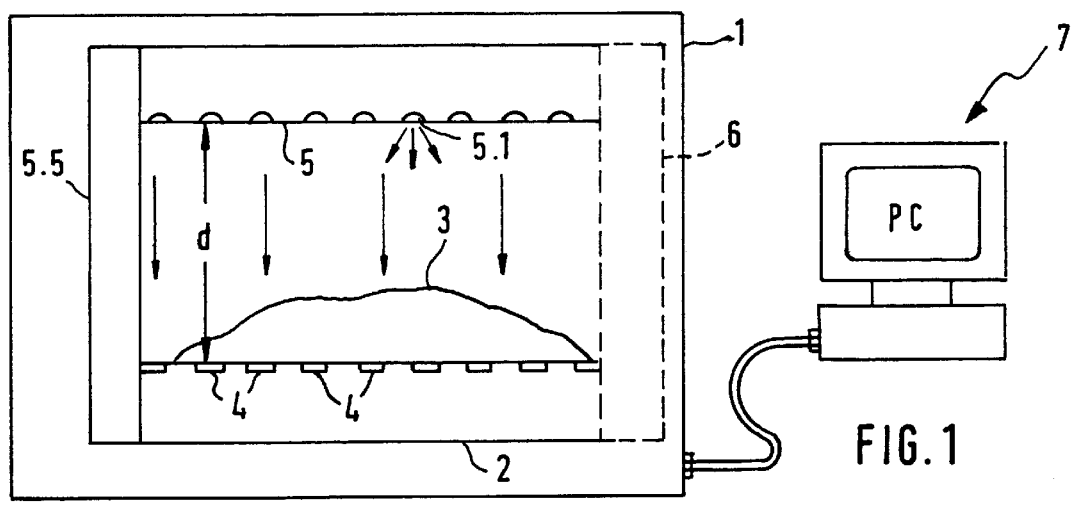
FIG. 1 shows schematically a measuring apparatus according to the invention which is coupled to a personal computer.

In FIG. 1, the block 1 comprises those parts of the measuring apparatus which are spatially associated with one another. These are a support 2 for the object 3, which may be a living cell, for example, and the sensors 4. Located at a distance d from the support 2 is an illuminant 5 consisting of individual sources of illumination 5.1 which are arranged in the same plane above the object. A homogeneous source of illumination is also possible, but individually activatable sources of illumination are advantageous, as will be shown in detail later. As a rule, the block 1 also includes an electronic controller 6, but this controller need not necessarily be within the block 1; it may also be located completely outside the block 1 or partly outside and partly inside the block. Some control functions may also be performed by the attached PC. It is particularly advantageous if the support 2, the sensors 4, and the controller 6 form a unit, because then at least a portion of the controller 6 has direct access to the sensors 4, whereby the number of electric signal and control leads to be brought out can be greatly reduced. Particularly suitable materials for the support 2 are semiconductor materials, such as silicon, since they exhibit good compatibility with living cells, which may necessitate taking suitable passivation measures, and since they allow the use of conventional fabrication processes for monolithic integrated circuits. As the support 2 will preferably be made of such semiconductor materials, the term "substrate", which is familiar from semiconductor technology, is used here for the support 2 for the sake of simplicity. The distance from the illuminant 5 to the support 2 can be changed by means of an electronically controllable actuator 5.5. The planes may be inclinable to each other so that slightly inclined structures can also be presented in the best possible way.

The immobilization and feeding of the one living cell 3, or the two or more living cells, on the support 2 are effected using methods and measures which are described in detail in the above-mentioned patent applications. The connections or devices necessary for this are not shown in FIG. 1. The measuring range of the measuring apparatus 1 is adapted essentially to the size of the living cell 3. The optical sensors 4, which are spaced as closely as possible, are at least one order of magnitude smaller than the cell; otherwise the optical resolution will become too poor. With the continuing miniaturization trend in sensor technology and the corresponding semiconductor technologies, this condition can be easily met. It is even conceivable that a resolution below the light wavelength can be achieved by the electrooptical near-field microscopy according to the invention. The illuminant is implemented, for example, with miniaturized light-emitting diodes 5.1, which are arranged in linear form or in the form of a matrix array. By sequential activation of the individual light-emitting diodes and sequential evaluation of the associated sensor signals, an analysis on the tomography principle can be made, so that a three-dimensional image of the cell 3 can be presented.

Figure 2:
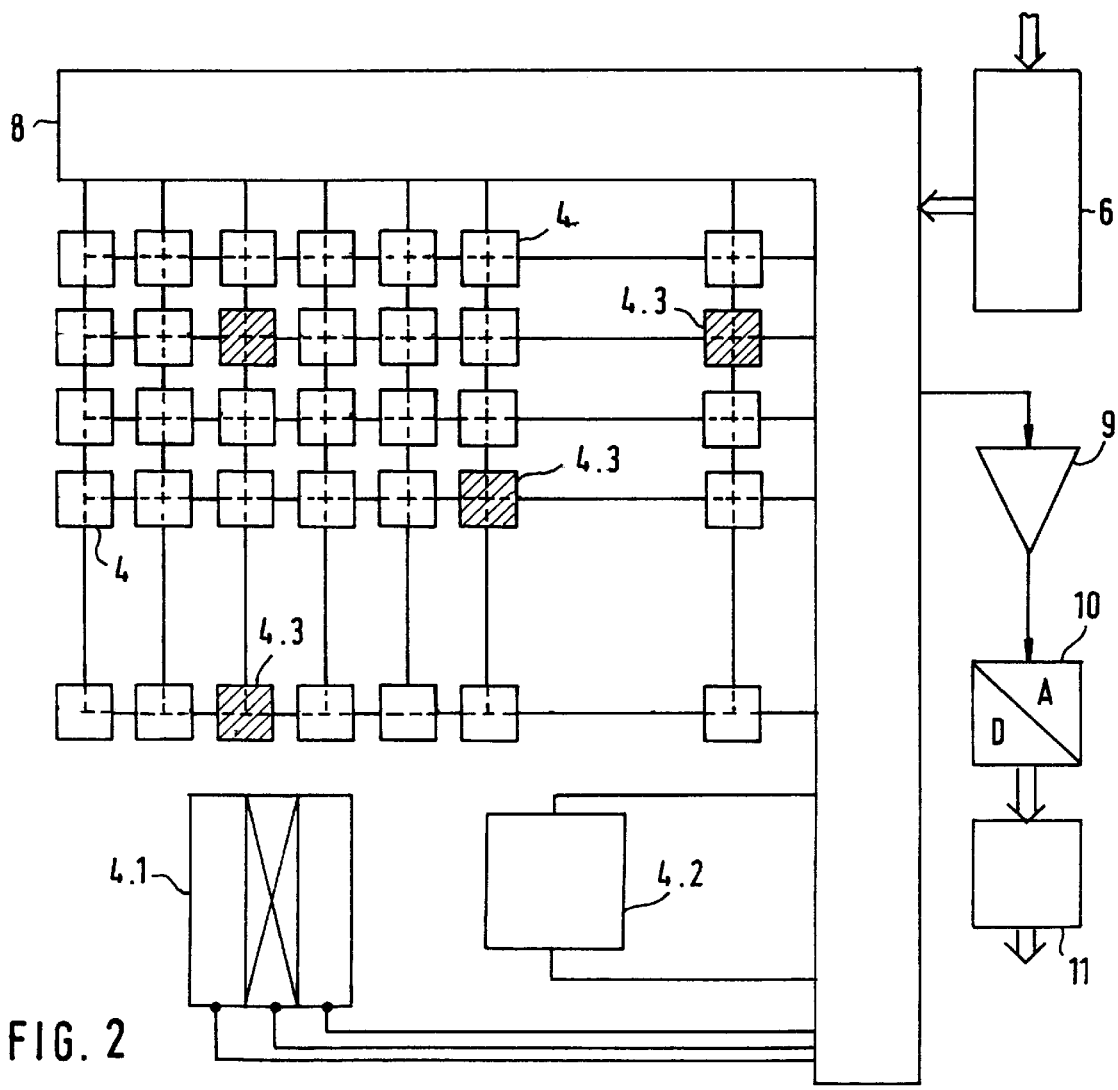
FIG. 2 is a schematical top view of a part of a sensor array with a plurality of optical and further sensors.

For the sake of clarity, only electrooptical sensors 4 are shown in FIG. 1. Determining as many physiological and/or chemical and/or physical parameters as possible requires corresponding ion-sensitive or material-sensitive sensors on the support 2 or in the vicinity thereof, cf., for example, the further sensors 4.1, 4.2 in FIG. 2. These sensors are implemented, for example, in the manner of field-effect transistors with and without gate terminals. The gate, and thus the current, is controlled essentially by the reaction of the overlying cell to different ambient conditions. In FIG. 2, these field-effect-transistor-like sensors 4.1, 4.2 are shown substantially greater than the optical sensors 4. They each occupy on the substrate an area approximately 15 microns square. If the miniaturization trend continues, however, these sensors 4.1, 4.2 can be made so small that they can be readily incorporated into the optical array, cf., for example, the sensors 4.3.

With the sensors 4.1, 4.2, which are either incorporated in the array of electrooptical sensors 4 or located in the immediate vicinity of this array, electronic signals can be picked off which provide information about the respective chemical and/or physiological condition of the object or the biological structure. The evaluation of these characterizing signals in conjunction with the electrooptical evaluation gives quick and unambiguous measurement results. By changing the environment of the cell 3, e.g., by adding physiologically active substances which interact with the metabolism of the cell, it can thus be quickly determined how the cell 3 or the object reacts to the added substances.

A schematic top view of the array of electrooptical sensors 4 is shown in FIG. 2. This matrix array permits selective sampling of the sensor outputs. All sensors are thus interrogated successively row by row and presented as corresponding picture elements on the screen of the PC. The sampling of the outputs of the individual sensors 4 is controlled by the switching facility 8, which is advantageously integrated on the same substrate. The switching facility 8 is connected by a bus to the controller 6, which in turn receives control signals from the attached PC. The controller 6 also serves as an interface circuit for converting the data from the PC into control signals for the switching facility 8, which forms the drive signals for the individual sensors 4, 4.1, 4.2, 4.3 and receives the reply signals from these sensors. The signals from the individual sensors are analog voltage or current values which generally have to be digitized before being further processed. This is advantageously done in connection with the switching facility 8 in the immediate vicinity of the sensors, because any signal corruption can thus be largely avoided. By means of an amplifier 9, the weak measurement signals are amplified before being digitized in an analog-to-digital converter 10. These data are then transferred out in parallel, serial, or mixed form via an output circuit 11. If a semiconductor material is used for the support 2, both the controller 6 and the input circuit 11 can be integrated on the same substrate. The two circuits 6, 11 may also cooperate with a common, bidirectional input/output circuit, whereby the number of leads to be brought out is further reduced. If the number of sensors is to permit sufficient optical resolution, intelligent preprocessing of the huge amount of data is necessary on the support 2, because the multitude of sensor signals to be analyzed could not be tapped from the support 2 for mechanical reasons alone, i.e., because of the cramped conditions.

In the array of optical sensors 4 of FIG. 2, some sensors 4.3 are represented by obliquely hatched blocks. These are either modified optical sensors 4, which are optimized for another wavelength, for example, or miniaturized sensors similar to the sensors 4.1, 4.2, which determine chemical and/or physiological and/or physical parameters of the cell 3.

Figure 3:
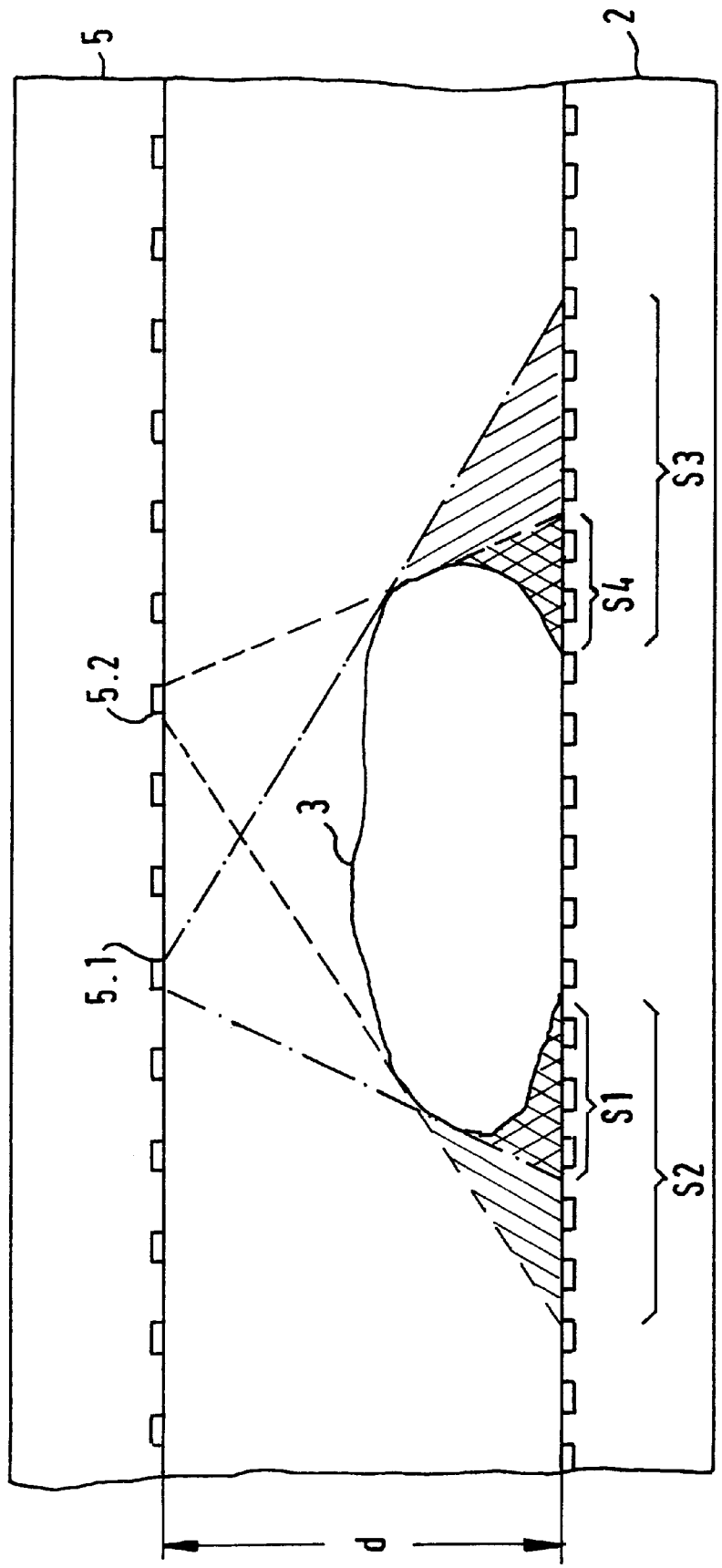
FIG. 3 is a schematic side view of a cell on the sensor array with different shadow zones.

A schematic side view of a cell 3 on the support 2 is shown in FIG. 3. Here, the cell does not cling so closely to the surface of the support as in FIG. 1. When the cell is illuminated by individual sources of radiation 5.1, 5.2 within the illuminant 5, different shadow zones S1, S2, S3, S4 are obtained in the edge region of the cell, which partly overlap, for example the shadow zones S1, S2 and the shadow zones S3, S4. At the optical sensors 4, the different shadow zones lead to different outline contours, which are stored and processed in the analyzing facility. Tomography-like representations can thus be obtained which provide information on the three-dimensional form of the cell and particularly on any changes of the form. An important criterion of the current condition of the cell 3 is the information on the extent to which the cell separates from its support. If the environment, including the support surface, is hospitable for epithelioid cells, such cells will try to cling to the support surface as closely as possible. If, however, the environment becomes unfavorable or even hostile to the cells, they will try to diminish their surface. To this end, they contract, until in the extreme case they become detached from the support and finally die. The contraction first takes place in the edge region and is therefore easy to determine from the above-described changes of the shadow zones S1 to S4.

A change of the shadow zone which can be evaluated as spatial information is also caused by a change in the distance d of the point source of radiation from the support. The change of the shadow zone is also observable if instead of the point sources of radiation, linear groups of sources of radiation are switched.

Monitoring the form of the cell in this manner is very efficient, since the effect of the substance to be examined on the condition of the cell can be checked already at the beginning of the addition of the substance or with weak concentrations, and one need not wait until irreversible damage to the cell or even death of the cell has occurred. In this initial phase, the cell reacts actively to the hostile substances and the condition is reversible when the medium surrounding the cell becomes more hospitable again. Thus, quick and reliable information is obtained on the effect of the substances to be examined on the cell. Through the gentle handling, the measuring apparatus 1 with the living cell 3 is available for further investigations. This permits a great number of individual investigations which would be very complicated and costly without the measuring apparatus according to the invention. The optical monitoring of the form of the cell in conjunction with the information from the other sensors is thus extremely efficient.

We claim:

1. A measuring apparatus (1) for measuring physiological and/or chemical and/or physical properties of at least one living cell (3) which is coupled with the measuring apparatus such that it is immobilized, the measuring apparatus comprising a plurality of sensors (4; 4.1, 4.2, 4.3) on a support (2) made of semiconductor material, wherein:
   at least some of the sensors are optical sensors (4) arranged in the form of a matrix array, with the size of the array being at least equal to that of the area on the support (2) which is to be occupied by one of the living cells (3);
   an electronic switching facility (8) is connected to the optical sensors (4) for selectively sampling the outputs of the optical sensors and feeding them to a signal-analyzing facility (7);
   the switching facility (8) receives control signals from a controller (6);
   an illuminant (5) coupled to the optical sensors (4), the illuminant producing a radiation field in the direction of the optical sensors (4), with the distance d of the illuminant from the optical sensors being at least such that the at least one living cell (3) on the support (2) is not hindered; and
   an electronically controlled actuator (5.5) for adjusting the distance d and/or the orientation of the illuminant (5) relative to the optical sensors (4).

2. A measuring apparatus (1) as claimed in claim 1, wherein the output signals from the optical sensors (4) are digitized by means of an analog-to-digital converter (10) implemented on the substrate.

3. A measuring apparatus (1) as claimed in claim 2, wherein the output signals from the analog-to-digital converter (10) are fed to a personal computer used as an external analyzing and reproduction facility.

4. A measuring apparatus (1) as claimed in claim 1, wherein the illuminant (5) includes a plurality of independently activatable sources of radiation (5.1; 5.1, 5.2) which are activatable singly or in groups by means of the controller (6).

5. A measuring apparatus (1) as claimed in claim 4, wherein the sources of radiation (5.1; 5.1, 5.2) are arranged in linear form.

6. A measuring apparatus (1) as claimed in claim 4 or 5, wherein the illuminant (5) and/or the optical sensors (4; 4.3) are continuously variable over their wavelength range or that their wavelength range is switch-selectable.

7. A measuring apparatus (1) as claimed in claim 4, wherein the sources of radiation (5.1; 5.1, 5.2) are arranged in the form of a matrix array.

8. A measuring apparatus (1) as claimed in claim 4, wherein by means of different activation schemes for the sources of radiation (5.1, 5.2), the three-dimensional form and/or the structural properties of the at least on living cell (3) are determinable.

9. A measuring apparatus (1) as claimed in claim 8, wherein the analyzing facility (7) automatically determines and analyzes two- and three-dimensional structural parameters of the cell geometry.

10. A measuring apparatus as claimed in claim 9, wherein the analyzing facility (7) reproduces the changes of the cell geometry in fast motion.

11. A measuring apparatus (1) as claimed in claim 1, wherein the optical sensors (4) are continuously variable over their wavelength range or that their wavelength range is switch-selectable.

12. A measuring apparatus (1) as claimed in claim 1, wherein in the area of the optical sensors (4; 4, 4.3) arranged in the form of a matrix array, further sensors (4.1, 4.2) are provided for making physiological and/or chemical and/or physical measurements on the at least one living cell (3) and/or on other living cells.

13. A measuring apparatus (1) as claimed in claim 12, wherein the further sensors (4.1, 4.2) in the area of the optical sensors (4, 4.3) are, at least in part, of different designs in order to measure different cell parameters.

14. A measuring apparatus (1) for measuring physiological and/or chemical and/or physical properties of at least one living cell (3) which is coupled with the measuring apparatus such that it is immobilized, the measuring apparatus comprising a plurality of sensors (4; 4.1, 4.2, 4.3) on a support (2) made of semiconductor material, wherein:
   at least some of the sensors are optical sensors (4) arranged in the form of a matrix array, with the size of the array being at least equal to that of the area on the support (2) which is to be occupied by one of the living cells (3);
   an electronic switching facility (8) is connected to the optical sensors (4) for selectively sampling the outputs of the optical sensors and feeding them to a signal-analyzing facility (7);
   the switching facility (8) receives control signals from a controller (6);
   an illuminant (5) coupled to the optical sensors (4), the illuminant producing a radiation field in the direction of the optical sensors (4), with the distance d of the illuminant from the optical sensors being at least such that the at least one living cell (3) on the support (2) is not hindered, wherein the illuminant (5) includes a plurality of independently activatable sources of radiation (5.1; 5.1, 5.2) which are activatable singly or in groups by means of the controller (6).

15. A measuring apparatus (1) as claimed in claim 14, wherein the sources of radiation (5.1; 5.1, 5.2) are arranged in linear form.

16. A measuring apparatus (1) as claimed in claim 14, wherein the sources of radiation (5.1; 5.1, 5.2) are arranged in the form of a matrix array.

17. A measuring apparatus (1) as claimed in claim 14, wherein by means of different activation schemes for the sources of radiation (5.1, 5.2), the three-dimensional form and/or the structural properties of the at least on living cell (3) are determinable.

* * * * *